United States Patent [19]

Kline

[11] Patent Number: 4,988,295

[45] Date of Patent: Jan. 29, 1991

[54] IDENTIFICATION MARKING SYSTEM FOR DENTAL INSTRUMENTS

[76] Inventor: Joseph M. Kline, 3501 N. Valley St., Arlington, Va. 22207

[21] Appl. No.: 471,267

[22] Filed: Jan. 26, 1990

[51] Int. Cl.[5] .............................................. A61C 3/00
[52] U.S. Cl. .................................. 433/141; 433/144; 40/913
[58] Field of Search ............... 433/141, 144, 143, 142, 433/102; 606/160, 167, 170; 40/913, 625

[56] References Cited

U.S. PATENT DOCUMENTS

| | | | |
|---|---|---|---|
| 171,106 | 12/1875 | Donaldson | 264/77 |
| 1,984,839 | 12/1934 | Murray | 40/2.2 |
| 3,251,150 | 5/1966 | Sedgwick et al. | 40/2.2 |
| 4,552,531 | 11/1985 | Martin | 40/913 |
| 4,671,916 | 6/1987 | Hamas | 264/249 |
| 4,882,867 | 11/1989 | Linden | 40/625 |

FOREIGN PATENT DOCUMENTS

2059778  4/1981  United Kingdom ................. 40/102

OTHER PUBLICATIONS

Catalog of Dixon Tool Co., Published in Newark, N.J., 1933.
Catalog of Suter, Published in 1-1-1981.
Textbook "Dental Instrument", 2-18-1983.

*Primary Examiner*—John Weiss
*Attorney, Agent, or Firm*—Dowell & Dowell

[57] ABSTRACT

Dental instruments including metallic curettes and scalers are provided with one or more annular rings which are formed in the handle of such instruments with the number of annular rings and their positioning with respect to the end of the handle indicating the appropriate instrument for use in treating the anterior and posterior, upper and lower, left and right, lingual and buccal tooth surface areas and also which reflect which block of an instrument is for use on distal and mesial surfaces.

6 Claims, 2 Drawing Sheets

IDENTIFICATION MARKING SYSTEM FOR DENTAL INSTRUMENTS

BACKGROUND OF THE INVENTION

1. Field of the Invention

This invention is generally directed to dental instruments and especially metallic scalers and curettes which may either be of a conventional hand held type or of an ultrasonic or vibrator type and more particularly to a method of identifying the size and angle of curvature of the cutting blades associated with such instruments by providing a physical annular marking on the handle of the instruments which marking will indicate to the practitioner which teeth and in which location of the patient's mouth a given instrument has been designed for use. More specifically, the present invention includes a marking system which will include forming a series of 1, 2 or 3 grooves or rings around the periphery of one end of the handle which rings will be spaced in relationship with respect to the end of the handle. The spacing of the rings with respect to one end of the handle will indicate first, whether the instrument is to be used on either anterior or posterior teeth as the rings will be spaced from one end of the handle with rings adjacent the end of the handle being to the anterior scalers and those toward the center of the handle being the posterior scalers; second, the rings will reflect which end of an instrument is to be used for treating distal or mesial surface areas; third, for posterior teeth (bicuspid to third molar), one or two rings will indicate which upper and lower lingual or buccal surfaces the instrument's cutting blades have been designed for; and fourth, three rings will designate scalers or curettes having specialized cutting blades.

2. History of the Related Art

Although many dental instruments including scalers and curettes would appear to have generally similar cutting blades associated therewith, in practice, the cutting blades may vary in size and configuration depending upon the area of the patient's mouth for which an instrument is specifically designed. More particularly, not only the length of the cutting blades but the angle of the cutting blades relative to the handle of an instrument will vary depending upon whether the implement is to be used on the distal or mesial surface or the buccal or lingual side of a tooth and will also vary depending upon whether the tooth is an anterior or posterior tooth. Further, the size of the tooth or roots will have an affect on the configuration of the cutting blades.

Due to the foregoing and in an effort to assist dental practitioners in the selection of proper scalers and curettes, most manufacturers provide a number which is applied to the handle of a dental implement to indicate the preferred area of use. The conventional numbering system employed is referred to as the Gracey System wherein low numbers such as 1-2 and 3-4 are used to indentify anterior teeth and larger numbers 11-12 and 13-14 the posterior bicuspid and molars. Unfortunately, such manufacturer numbered markings are not easily visible as most numbers are simply stamped into small areas or one side of the handle of an implement with such numbers being visible only upon careful examination of the entire periphery of the instrument handle. In view of the foregoing, it is difficult for a dental practitioner to visually inspect the blades or numbers associated with a group of instruments which are located in side-by-side relationship with respect to one another and easily identify the instrument which is necessary for scaling or curetting a particular tooth or root surface within a patient's mouth.

In order to overcome such difficulties, it has been proposed, such as in Linden U.S. Pat. No. 4,882,867 to mold the handles of dental instruments to incorporate in the handle sleeves or rings of different colored material which will extend outwardly from the handle to indicate the type of instrument. This document also discusses that in the past, attempts have been made to color portions of dental instrument handles in order to indicate the function for which an instrument is to be utilized In the patent it is noted that, during repeated sterilizations, such colorized markings are frequently destroyed and therefore are not effective for prolonged use.

The use of molded components in a dental instrument handle is also not practical. Such molded components may be raised with respect to the surface of the handle of an instrument and thereby interfere with the use of such an instrument. Also, as such an instrument must be repeatedly sterilized, it is preferred that it be formed of metallic material with the handles, shanks and blades be as continuous as possible and nonporous. With a molded instrument, the handle will be made of a composite plastic material which is not as suitable for repeated usages in a sterilized environment. Such molded structures may develop minute cracks or separations in which viruses, bacteria and germs may be harbored. Further, such a marking system is not efficient in allowing more conventional metallic dental instruments to be marked without requiring a complete modification of the handles associated with such instruments. Therefore, such a marking system is not practical when considering the number of manufacturers and the general preference for all metallic instruments to meet today's requirements of complete sterilization.

In areas outside of dentistry, it has been proposed to mark the handles of metallic tools for purposes of identification. In U.S. Pat. No. 1,984,839 to Murray, a marking system for identifying drill bits is disclosed wherein painted grooves are applied in the surface of the tool with the color of the groove indicating relative sizes of the drill bits. As with prior art dental marking systems utilizing a painted surface to indicate the size or function of an instrument, such a marking system is not conducive for use in dentistry where the dental instruments must be repeatedly sterilized which process would ultimately deteriorate the colored markings associated with such instruments.

Additional examples of marking systems for tools are disclosed in Hamas et al. U.S. Pat. No. 4,671,916 to and Sedgwick U.S. Pat. No. 3,251,150.

SUMMARY OF THE INVENTION

This invention is directed to a system for identifying dental instruments and more specifically to the method of marking the handle of dental scalers and curettes by applying a series of one, two or three rings about the periphery of the instrument handle with such rings being spaced in relationship to the end of the handle. The number of rings and spacing indicating the area of use and general size of teeth or roots for which the given instrument has been manufactured. The annular rings or grooves will be formed in the peripheral surface of the metallic handle associated with such dental instruments with a single ring indicating instruments which may be utilized on teeth from the centrals to the third molars and on the upper left and lower right buccal and lower left and upper right lingual surfaces. Double rings will indicate instruments to be used on teeth from the centrals to the third molars and on upper left and lower right linguals and lower left and upper right buccal surfaces. If preferred, the designation associated with the single and double rings could be reversed. The three rings would indicate instruments having special blades for use on anterior and posterior tooth surfaces.

In addition to the foregoing, the rings will be made adjacent to one end of the instrument handle. The rings are preferably placed adjacent the end from which the cutting blade for use on distal tooth surfaces extends. The cutting blade carried at the opposite end of the handle is for use with mesial tooth surfaces. This designation could be reversed, if desired.

In each embodiment, whether one, two or three rings are provided on an instrument handle, the spacing of the rings relative to the end of the handle will indicate the general area of use for the cutting blades associated with the instrument. In this respect, rings closest to the end of a handle would indicate the instrument has a cutting blade suitable for smaller tooth and root surfaces and will generally correspond to the 1-2 scalers or curettes defined by the Gracey numbering system. Rings spaced closer to the center of the handle would indicate that the cutting blades of the instrument are to be utilized on larger tooth and root surfaces and will generally correspond to the 13-14 scalers and curettes defined by the Gracey numbering system. If preferred, the system could be reversed so that rings indicated on the exterior portion of the handle could indicate instruments designed for use on larger teeth with rings being placed on the inner portion of the handle indicating instruments having cutting blades which are designed for use on smaller teeth.

It is the primary object of the present invention to provide a system for marking metallic dental instruments and especially scalers and curettes in such a manner that the instruments may be easily identified as to an area of specific use within a patient's mouth and which will also identify the general teeth or roots for which a given instrument is particularly suited.

It is a further object of the present invention to provide a system for marking metallic dental scalers and curettes wherein the markings will be easily indentifiable without requiring an intensive visual inspection of the dental instrument in order to determine either the posterior or anterior, the lingual or buccal, or the mesial and distal surface area for which the instrument is specifically designed.

It is also an object of the present invention to provide a system for marking dental instruments wherein the marking system will not interfere with the normal use of the instrument during patient treatment and wherein the markings cannot be removed after repeated instrument sterilizations.

It is another object of the present invention to provide a system for marking dental instruments which will not be affected by, nor be detrimental to, complete and repeated instrument sterilizations.

DESCRIPTION OF THE PREFERRED EMBODIMENT

With continued reference to the drawings, the dental implement identification and marking system of the present invention will be described in greater detail. In describing the preferred embodiment, it should be remembered that although the markings will be described as indicating various features of the dental instruments, depending upon whether one, two or three rings are formed in the handle of the instruments, it is envisioned that any variation in identifying the various structures and features of the implements utilizing the one to three rings can be made and still be within the teachings of the present invention. That is to say, although the invention will be described with one ring defining a particular meaning, and two rings defining a second meaning, it is envisioned that these meanings could be reversed so that the first or second rings may be used to create the opposite meaning. It is important however, that the identification system provide for a readily apparent identification of not only the anterior or posterior area of the patient's mouth for which an implement is designed but also that the markings provide an immediate indication of the mesial and distal approach for use with a cutting blade and the general area of the patient's mouth for which the cutting blade has been designed.

Figure 1:
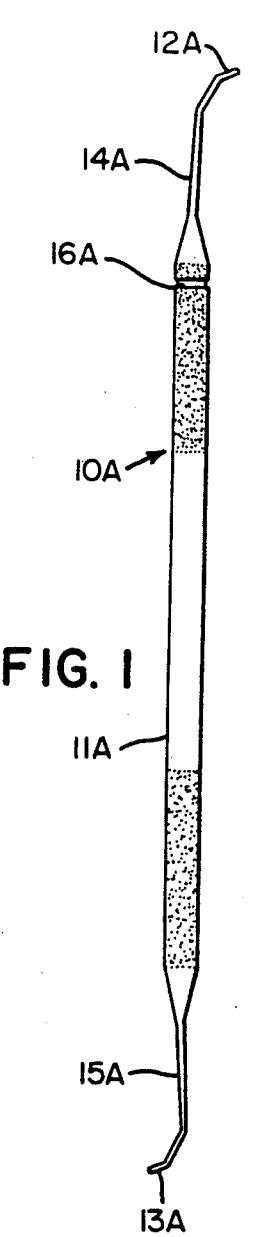
FIGS. 1-3 are perspective views illustrating the marking system of the present invention wherein a single ring is utilized around the handle of each instrument to indicate which end of the instrument to be used for either a mesial or distal approach and also the upper and lower lingual and buccal surfaces of anterior and posterior teeth for which the instrument is designed for use. In each Figure, the single rings are spaced at different locations with respect to the end of the instrument handle to indicate the general area on which teeth or roots for which the instrument is designed by directly reflecting that the instrument is comparable to a specific Gracey number.
Figure 2:
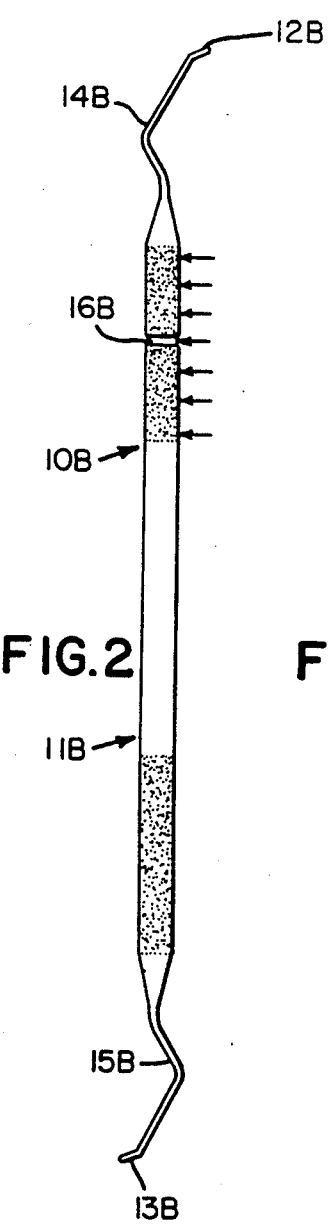
Figure 3:
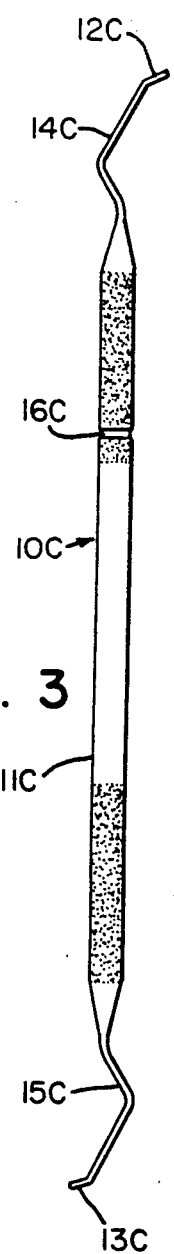

With reference to FIGS. 1-3, three scalers 10A, 10B and 10C are shown each of which includes a handle portion 11A, 11B and 11C. Each instrument includes a pair of oppositely oriented cutting blades 12A-C and 13A-C respectively.

As shown, each instrument is provided with a single ring or band 16A-C which is formed in the metal handles in spaced relationship from the shanks 14A-C. In accordance with the marking system, the single rings indicate that the instruments 10A-C are specifically designed for use on anterior and posterior teeth including the centrals to the third molars. More specifically, instruments 10A-C are designed for use on the upper left and lower right buccal, and lower left and upper right lingual tooth surfaces, both mesial and distal. The blade in closest proximity to the ring or band will be the blade used on distal surfaces with the opposite blade being used on mesial surfaces.

In addition to the foregoing, the relative spacing of the rings 16A-C from the shanks 14A-C will generally indicate the corresponding Gracey number of the instrument and therefore will give the practitioner guidance as to which specific tooth and root area instruments should be used on. Generally, the closer the ring to the shank, the lower the Gracey number thus indicating anteroir usage. It is preferred that the spacing of the rings correspond somewhat, though not exactly, to the conventional Gracey numbering system so that instrument 10A will generally correspond to a 1-2 Gracey instrument; instrument 10B will generally correspond to a 13-14 Gracey instrument.

It should be noted that the conventional Gracey numbering system includes seven (7) size classifications, there being 1-2, 3-4, 5-6, 7-8, 9-10, 11-12, and 13-14. The drawings only reflect markings for the 1-2, 7-8 and 13-14 instruments. The ring spacing for all the numbers is indicated by the arrows in FIG. 2.

In view of the foregoing, instrument 10A is designed for small tooth and root areas such as anterior teeth; instrument 10B is designed for use intermediate posterior tooth and root areas; and instrument 10C is designed for use on larger posterior surface areas such as the first molars.

As previously noted, the relative spacing of the rings 16A-C may indicate a reverse designation with 16A indicating the instrument for use on posterior tooth surfaces (Gracey 13-14) and 16C on the smaller anterior tooth surfaces (Gracey 1-2). Also, the end of the instrument on which the rings are located could indicate the adjacent blade is for mesial as opposed to distal surfaces.

Figure 4:
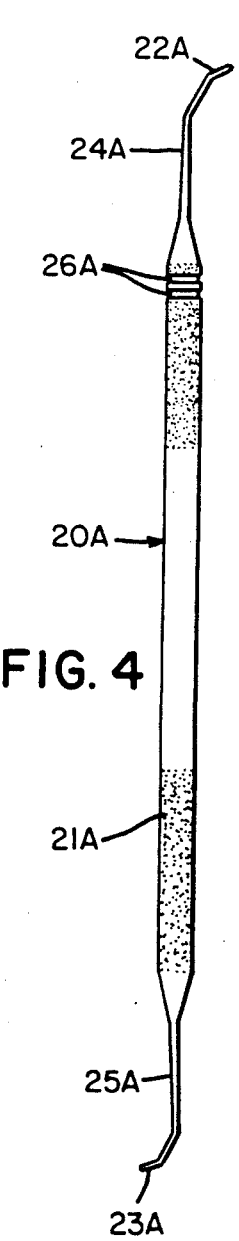
FIGS. 4-6 are perspective views illustrating the marking system of the present invention incorporating double rings to indicate the end of the instrument to be used for either a mesial or distal approach and also which upper and lower buccal or lingual surface of anterior and posterior teeth for which the instrument is designed for use. In each Figure, the double rings are spaced at various locations from the end of the instrument handle in order to indicate the general area or which teeth or roots are to be treated by reflecting the related Gracey number.
Figure 5:
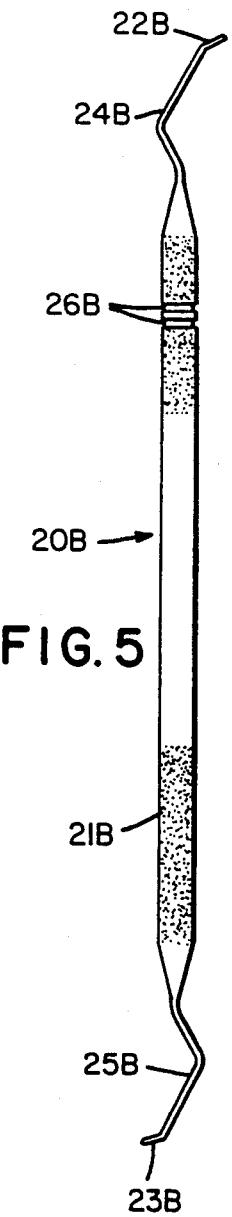
Figure 6:
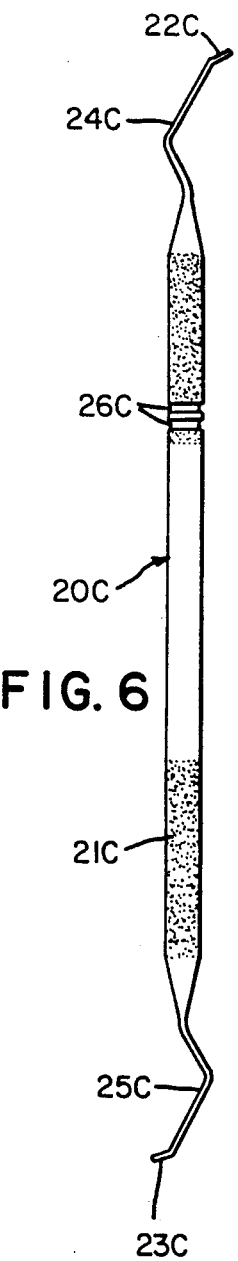

With reference to FIGS. 4-6, three scalers or curettes 20A, 20B and 20C are shown each of which includes a handle portion 21A, 21B and 21C. Each instrument also includes a pair of oppositely oriented cutting blades 22A-C and 23A-C, respectively which are mounted to their respective handles by way of shanks 24A-C and 25A-C. As shown, each instrument is provided with a double ring or set of bands 26A-C which are formed in the metal handles in spaced relationship from the shanks 24A-C. In accordance with the marking system, the double rings indicate that the instruments 20A-C are specifically designed for use on anterior and posterior teeth from the centrals to the third molars. Unlike the instruments shown in FIGS. 10A-C, however, instruments 20A-C are designed for use on the upper left and lower right lingual, and lower left and upper right buccal tooth surfaces, both mesial and distal. The blade in closest proximity to the double rings or bands will be the blade used on distal surfaces with the opposite blade being used on mesial surfaces.

In addition to the foregoing, and as was the case for instruments 10A-C the relative spacing of the double rings 26A-C from the shanks 24A-C will indicate a similar Gracey number for the instrument and thus will reflect the general anterior or posterior arc of use. Therefore, the practitioner will have guidance as to the specific tooth and root areas for which the instrument is to be used. Generally, the closer the rings to the shank, the lower the Gracey number and thus the smaller the surface to be treated. Therefore, instrument 20A is designed for small anterior tooth and root areas; instrument 20B is designed for use on intermediate posterior tooth surface areas; and instrument 20C is designed for use on larger posterior surface areas such as the first molars.

As with the previous embodiment, the relative spacing of the rings 26A-C may indicate a reverse designation with regard to the area of use of the blades and also the placement of the rings adjacent to one end of the handle could reflect that the adjacent blade is for the mesial as opposed to distal surfaces.

Figure 7:
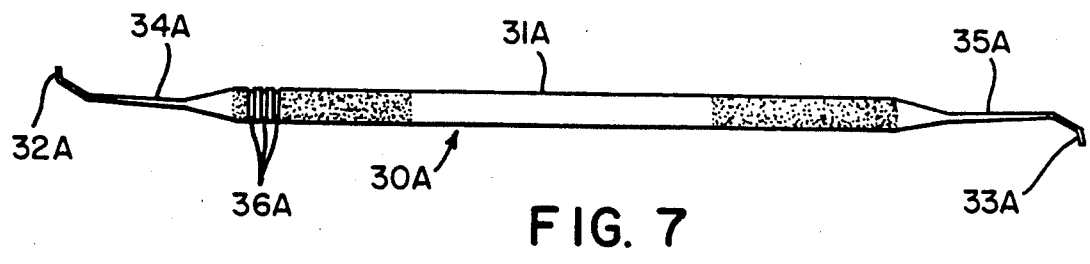
FIGS. 7 and 8 are perspective views illustrating a three ring marking of the present invention with the ring markings indicating an instrument having specialized blades for use on various anterior and posterior teeth with the markings spaced adjacent to the end of the handle designating blades for smaller tooth surface areas such as anterior teeth and with the relative spacing of the bands from the end of the handle being indicative of cutting blade sizes for use on posterior teeth.
Figure 8:
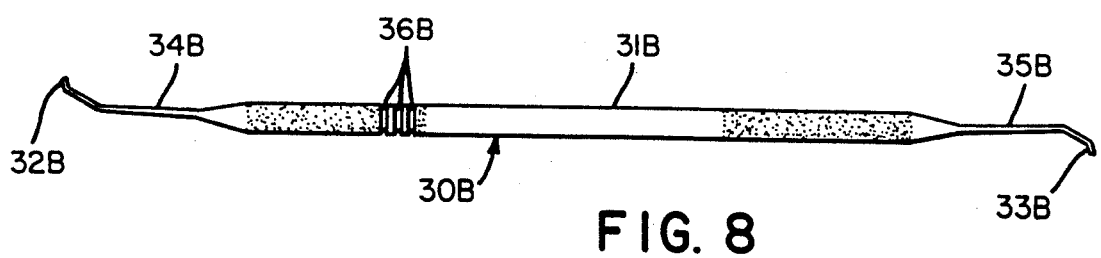

With reference to FIG. 7 and 8 two scalers 30A and 30B are shown, each of which includes a handle portion 31A and 31B. Each instrument further includes a pair of oppositely oriented cutting blades 32A and 32B and 33A and 33B which are mounted to their respective handles by way of shanks 34A and 34B and 35A and 35B, respectively. As shown, each instrument is provided with a triple ring or series of bands 36A and 36B which are formed in the metal handles in spaced relationship from the shanks 34A and 34B. In accordance with the marking system, the triple rings indicate that the instruments 30A and 30B have specialized cutting blades such as described in applicant's concurrently filed application entitled Scalers For Periodontal Use or include extra long or short shanks or heavy duty scalers and the like. As with the prior instruments 10A-C and 20A-C, the relative spacing of the triple rings with respect to the shanks 34A and 34B designates the general area of use of the cutting blades. In the preferred embodiment, the closer the triple rings are to the shank, the larger the tooth surface areas. Therefore, instrument 30A is designed for use on larger posterior tooth surfaces whereas the smaller cutting blades of the instrument shown in FIG. 8 are designed for smaller surface areas such as anterior teeth.

As with the instruments 10A-C and 20A-C, the end of the instrument upon which the triple rings are provided designates either to the mesial or distal approach. Therefore, the cutting blade adjacent the end of the instrument on which the rings are formed will be utilized for the distal approach whereas the opposite cutting blade will be used for the mesial approach. As with the prior markings, the reverse designations could be utilized.

In the use of the markings system of the present invention, the series of rings will not only indicate to the practitioner the general Gracey designation of an instrument and thus whether or not a specific instrument is designed for anterior or posterior use but the number of rings will indicate to the practitioner which lingual or buccal surface of an instrument is designed for.

Utilizing the marking system of the present invention, a proper instrument may be easily recognized from a group of instruments assembled in one area and therefore will greatly enhance the ability of the practitioner to choose a proper scaler or curette for a specific area to be treated as for use in a specific treatment.

Although the numbering system of the invention has been described for use with double bladed instruments, it should be noted that single blade instruments could be marked with the series of one, two or three rings. In such uses, fourteen (14) sizes of instruments are standard. Therefore, the rings would be spaced at fourteen different intervals from the shank adjacent the blade to indicate the general area of use of the instrument. Also, the markings of the present invention may be altered as to meaning to fit a given practitioner.

It should further be noted that instruments such as shown at 10A which are for use on anterior teeth are also well suited for scaling posterior buccal and lingual surfaces. In this respect, anterior scalers have the finest tip, not pointed, just barely rounded and turned slightly upward to give a bladed spoon effect to remove debris under fine gum margins. The ends of scaler blades get wider as they proceed posteriorly in the mouth to thereby create a greater spoon effect for cleaning out bifurcations of root areas.

I claim:

1. A marking system for dental implements including scalers and curettes in which the implements have handles having a first cutting blade extending from one end and which blade is mounted to the handle by a first shank and wherein the implement is constructed of a metallic material comprising, at least one ring being provided in the instrument handle in spaced relationship with respect to the shank, and wherein the relative spacing of the at least one ring relative to the shank will indicate the general area of use of the first cutting blade.

2. In the dental instrument of claim 1 including a second cutting blade mounted adjacent the opposite end of the implement handle by a second shank, said at least one ring being provided adjacent to the first shank which connects the first cutting blade to the instrument handle to thereby indicate that said first cutting blade is either to be used on a mesial or distal surface of a tooth.

3. A method for marking dental instruments such as scalers and curettes wherein the implements include instrument handles having opposing blades mounted to opposite ends of the handles and which are connected to the handles by intermediate shanks comprising the steps of providing at least one ring the surface of the handle adjacent one of the shanks to thereby indicate that the adjacent cutting blade is either for use on mesial or distal surfaces of a tooth and wherein said one and two rings will indicate that the instrument is for use on anterior and posterior teeth from the central to the third molars and wherein the spacing of the rings relative to the adjacent shank will indicate the general size of cutting blade.

4. A method for marking dental implements including scalers and curettes wherein the dental implements include handles having opposing blades mounted thereto by intermediate shank portions and wherein the dental implements have varying sizes of shanks and cutting blades for use on different teeth within a patient's mouth comprising the steps of:

A. Providing one ring in the implement handles of dental implements adjacent one of said shank portions to indicate that the adjacent blade is for use on either mesial or distal surfaces and that the opposite blade is for use on the other of said mesial or distal surfaces and further to indicate that the implement is for use on anterior or posterior teeth including the upper left and lower right buccal, and lower left and upper right lingual surfaces of a patient's teeth;

B marking dental implements for use on anterior and posterior teeth with a pair of rings in the implement handle adjacent one of the shank portions to indicate that the adjacent blade is for use on either mesial or distal surfaces and the opposite blade is for use on the other of said mesial or distal surfaces and further to indicate that the implement is for use on the upper right and lower right lingual and lower left and upper right buccal surfaces of a patient's teeth;

C. and marking implements having special cutting blades with three rings in the handle adjacent one of the shank portions 5. The method of claim 4 wherein the relative spacing of the rings from the adjacent shank portion will indicate the general size of the cutting blades associated therewith.

6. The method of claim 5 in which the relative spacing of the rings will correspond to instrument numbers according to the GRACEY system.

* * * * *